United States Patent [19]
Demetriou et al.

[11] Patent Number: 6,140,123
[45] Date of Patent: Oct. 31, 2000

[54] METHOD FOR CONDITIONING AND CRYOPRESERVING CELLS

[75] Inventors: Achilles A. Demetriou, Bel Aire; Andreas Kamlot, Los Angeles; Jacek Rozga, West Lake Village, all of Calif.

[73] Assignee: Cedars-Sinai Medical Center, Los Angeles, Calif.

[21] Appl. No.: 09/168,366

[22] Filed: Oct. 7, 1998

[51] Int. Cl.[7] .......................... A01N 63/00; A01N 65/00; C12N 1/00; C12N 1/02; C12N 5/00
[52] U.S. Cl. .......................... 435/374; 424/93.1; 435/243; 435/260; 435/261; 435/325; 435/404
[58] Field of Search .......................... 424/93.1; 435/325, 435/243, 260, 261, 374, 404

[56] References Cited

U.S. PATENT DOCUMENTS

| | | | |
|---|---|---|---|
| 4,004,975 | 1/1977 | Lionetti et al. | 195/1.8 |
| 4,559,298 | 12/1985 | Fahy | 435/1 |
| 4,890,457 | 1/1990 | McNally et al. | 62/65 |
| 4,965,185 | 10/1990 | Grischenko et al. | 435/1 |
| 4,980,277 | 12/1990 | Junnila | 435/2 |
| 5,171,660 | 12/1992 | Carpenter et al. | 435/1 |
| 5,328,821 | 7/1994 | Fisher et al. | 435/1 |
| 5,336,616 | 8/1994 | Livesey et al. | 435/240.2 |
| 5,358,844 | 10/1994 | Stossel et al. | 435/2 |
| 5,364,756 | 11/1994 | Livesey et al. | 435/2 |
| 5,378,601 | 1/1995 | Gepner-Puszkin | 435/2 |
| 5,424,207 | 6/1995 | Carpenter et al. | 435/260 |
| 5,504,002 | 4/1996 | Aoyagi | 435/240.2 |

*Primary Examiner*—David M. Naff
*Assistant Examiner*—Deborah K. Wave
*Attorney, Agent, or Firm*—Pretty, Schroeder & Poplawski

[57] ABSTRACT

A method is provided for preconditioning and cryopreservation of cells harvested from a donor. Cells are suspended in a cell conditioning and cryopreservation medium containing a cryopreservative such as Dimethyl Sulfoxide (DMSO) and the suspension is incubated for a period of at least ten minutes and the cells are frozen. The medium includes adenosine, a calcium channel blocker, and a cell nutrient matrix comprising a sufficient amount of cell nutrients to sustain the metabolic needs of the cells during incubation without producing detectable levels of lactate or substantially depleting the nutrient substrates to maintain viability of the harvested cells. In some embodiments, a cryopreservative is added step-wise before the cell suspension is frozen and removed step-wise after the cell suspension is thawed.

46 Claims, No Drawings

METHOD FOR CONDITIONING AND CRYOPRESERVING CELLS

BACKGROUND OF THE INVENTION

1. Field of the Invention

This invention is related generally to a method for the preservation of viable cells and in particular to a method for the preconditioning and long term storage of viable cells.

2. Discussion of the Related Art

The preservation of viable cells which have been harvested from a donor source is of great importance and utility in the scientific and medical communities. Indeed, cells which have been harvested and preserved are routinely used in scientific research and development. For instance, preserved cells are often tested to aid in the development of medical treatments or to provide information on physical or chemical properties of the cells. Further, a collection of readily available viable cells allows scientists to conduct experiments at times which are suitable to laboratory availability or the researcher's schedule. To be useful, the preserved cells must retain the integrity and viability of the cells at the time of harvest. Thus, the process of preserving the cells must not, in itself, damage or destroy the cells.

In conventional cryopreservation techniques, cells are harvested, suspended in a storage solution, then preserved by freezing. When the cells are to be used, they are thawed, for example, cells taken from human donor sources are brought back to the normal human body temperature (i.e., approximately 37° C.), and then placed in a cell culture medium. Cryopreservation protocols subject the cells to a multitude of stresses and insults throughout the process of cell harvesting, freezing, and thawing. These stresses and insults can cause irreparable damage to the cell.

Ischemia, a lack of blood flow, occurs as soon as the life of the cell's donor is terminated. Immediately thereafter, the cell experiences hypoxia, or oxygen deprivation, due to the lack of blood flow. Hypoxia causes anaerobic metabolism in normally aerobic cells. Anaerobic metabolism produces toxic byproducts, such as the build-up of lactic acid (acidosis). Some of the byproducts of anaerobic metabolism produce oxygen free-radicals that damage or destroy the cells when the cells are reoxygenated. Accordingly, prior to taking a tissue sample, the temperature of the donor source is reduced such that metabolic activity in the cells of the donor source is minimized. Reduction of temperature of the donor source reduces the energy state of the cells which aids in reducing the affects of ischemia and hypoxia. Typically, the temperature of the donor source is lowered to 4° C. Although some residual metabolic activity exists in the cells at 4° C., 4° C. is about the lowest temperature available which does not cause the formation of ice crystals on the cells.

The cells are typically isolated from the tissue sample by addition of a hydrolytic enzyme. The hydrolytic enzyme deteriorates the extracellular tissue structure, thus causing the release of the desired cells. Unfortunately, the hydrolytic enzyme also harms the isolated cells. Some of the cells are destroyed during isolation. Other cells are weakened by exposure to the hydrolytic enzyme. It is believed that cells weakened by such enzymatic insult are less viable.

Once the cells are harvested, the cells are suspended in a storage solution which is also, typically, at 4° C. One example of a widely used cell storage medium is Dulbecco's Modified Eagle Medium ("DMEM"), an aqueous solution containing 10 wt. % fetal calf serum and low levels of glucose. DMEM is intended to provide support for the minimal metabolic activity which occurs just before the cells are frozen and just after the cells are brought to normal body temperature. Because cells are frozen as soon after harvest as possible, in order to completely arrest cell metabolism, the amount of glucose needed to support metabolic activity is quite low.

The harvested cells can also be harmed by the initial freezing and the subsequent thawing of the cell suspension. The cell membranes can be damaged primarily due to the rapid change in osmotic pressure that results when liquid inside or outside the cell is frozen or thawed. Freezing and thawing of the cell suspension causes a dramatic change in the concentration of liquid on one side of the membrane relative to the other. The dramatic change in concentration creates an osmotic pressure differential. The transmembrane pressure differential causes liquid to flow into the cell or liquid in the cell to flow out of the cell to reach equilibrium osmotic pressure. When excess liquid flows into a cell, the cells burst. When too much liquid leaves a cell, the cell shrivels and dies.

It is known to add cryopreservatives to a cell storage medium, such as DMEM, to prevent cell damage during freezing. Cryopreservatives include dimethyl sulfoxide (DMSO), glycerol, propylene glycol, and other large molecules with a high bonding affinity to water. Cryopreservatives are absorbed into the cells and have sufficient size that they are not likely to be rapidly transported across the membrane. Thus, when osmotic pressures change, the water remains bound to the cryopreservative and is stabilized to the change in transmembrane osmotic pressure. Of all the cryopreservatives, DMSO is by far the most preferred because of its high bonding affinity to water. However, DMSO is toxic to cells if added when the cells are at normal body temperature, and it is, generally, rapidly added to the cells just before the cells are frozen, i.e., when the temperature of the cells has been lowered to approximately 4° C. Furthermore, the cells must be carefully washed to remove DMSO after the cells are subsequently thawed to a temperature of about 4° C.

In addition to the above-stated problems, current preservation protocols are limited in that they are not necessarily transferrable between samples. Indeed, the type of sample has, in part, dictated the requirements of the preservation technique such that the technique employed is dependent, in part, upon the sample to be stored. Examples of various techniques of freezing and thawing of different sample types are found, for example, in U.S. Pat. No. 4,004,975 to Lionetti et al., directed to freezing and thawing of human white cells; U.S. Pat. No. 4,890,457 to McNally et al., directed to the freezing and thawing of collagen-rich tissue, such as heart valves; and U.S. Pat. No. 4,965,185 to Grischenko et al., directed to the freezing and thawing of embryos, more specifically, mammal embryos.

U.S. Pat. No. 5,328,821 to Fischer et al. discloses a cryopreservation solution for tissue slices. The solution contains (a) glucose and (b) a cryopreservative. Other ingredients include (c) impermeates, such as potassium gluconate, potassium saccharate, and mannitol, to prevent or minimize hypothermic induced cell swelling, (d) hydrogen ion buffers, such as a phosphate, (e) adenosine, an adenine triphosphate ("ATP") precursor for the regeneration of high energy phosphate compounds, (f) free-radical inhibitors, such as allopurinol and mannitol, (g) reducing agents, such as glutathione, (h) inorganic salts, such as KCl, $MgSO_4$, MgCl, $NaHCO_3$, and $KHCO_3$, (i) vitamins, such as vitamin E and vitamin C, (j) hormones, such as dexamethasone and insulin, (k) calcium channel blockers, such as verapamil, and (l) acid generating substrates, such as succinate, fructose and glucose. One of the drawbacks of the cell cryopreservation solution described in the Fischer et al. patent is that its use is limited to cryopreservation of tissue slices. Consequently, the utility of the solution disclosed in the Fischer patent has unproven effectiveness with harvested cells that have been weakened because they have been isolated by treatment with a hydrolytic enzyme.

Although some cryopreservation protocols have altered the conventional methods, these altered methods have failed to address all of the above mentioned problems. For instance, U.S. Pat. Nos. 5,171,660 and 5,424,207, both to Carpenter et al., describe an alternative to the immediate freezing of tissue samples. These patents give examples of placing heart leaflets in DMEM and then preincubating the tissue, for from about 5 minutes to about 24 hours, at a temperature of from about 27° C. to about 42° C. The preincubation is said to assure that the metabolic energy status and functional capacity of the tissue are restored when the tissue is thawed.

In U.S. Pat. No. 4,559,298 to Fahy, directed to vitrification of biological material, the cryopreservative is introduced and removed in step-wise concentrations. Specifically, the method in Fahy uses step-wise concentrations of greater than 10% per step. The large step-wise additions are aimed at inhibiting re-establishment of the isotonic volume of the cells prior to vitrification, i.e., osmotic equilibrium of the cells is not desired. Further, despite the step-wise addition and removal of a cryopreservative, intra-cellular concentrations are about 30% which is too high of a concentration and is not acceptable for some sample types, such as, for example, eukaryotes and aerobic prokaryotes. In U.S. Pat. No. 4,890,457 to McNally et al., which is directed toward collagen-rich tissue, the cryopreservative, DMSO, is removed in a 2.5% step-wise concentration. Nonetheless, the cryopreservative is not introduced in the same gradual step-wise concentrations, thus, potentially introducing cell stresses prior to freezing.

Thus, there remains a need for a generally applicable method for cell cryopreservation that more effectively maintains the integrity, viability and function of all types of cells during the cryopreservation process, more specifically, eukaryote, and aerobic prokaryote cells. The present invention satisfies these and other needs and provides further related advantages.

SUMMARY OF THE INVENTION

Now in accordance with this invention, there has been found a generally applicable method for cell cryopreservation that more effectively maintains the integrity, viability, and function of all types of cells and, in particular, eukaryote and aerobic prokaryote cells. Embodiments of the method comprise the steps of harvesting the desired cells, suspending the cells using a cell conditioning and cryopreservation medium as a storage medium, freezing the cells, and thawing the cells, and further comprise the steps of preconditioning the cell suspension prior to freezing and, in some embodiments, post conditioning the cell suspension after thawing.

In some embodiments of the inventive method, the donor source is maintained at a warm temperature, typically between about 34° C.–38° C., when the cells are initially harvested. An advantage to maintaining the cell donor source at a warm temperature is that the metabolism of the cells are maintained at a high level which assists in reducing stress to the cells and decreases the risk of damage during subsequent harvesting, freezing, and thawing.

In accordance with the inventive method, cells are harvested and then a suspension of the cells incubated at a temperature of from about 34° C. to about 38° C., preferably, about 37° C. for a fixed period of time, ranging from about 10 minutes to 48 hours, preferably from about 15 minutes to about 2 hours, and more preferably about 25 minutes, in the cell conditioning and cryopreservation medium. In some embodiments, the cell suspension is oxygenated by bubbling oxygen through the suspension using a gas having an oxygen content of no less than 80 vol. %. In a preferred embodiment of the inventive method, the cell conditioning and cryopreservation medium contains adenosine, a calcium channel blocker, and sufficient metabolic substrates to maintain cell integrity, viability, and function in all phases of the conditioning and cryopreservation process. One advantage of preconditioning is that the cells are aided in reversing the damage inflicted through harvesting. Another advantage is that preconditioning allows the cells time to restore their energy levels after harvesting and prior to being frozen.

In some preferred embodiments of the instant invention, a cryopreservative is gradually added to and removed from the cells. One advantage of gradually adding and removing the cryopreservative is that the osmotic equilibrium of the cells is maintained, thereby, preventing damage to the cells by swelling or shrinkage. For example, after preconditioning, the temperature of the cell suspension is reduced, followed by a step-wise treatment of the cells in which a storage solution, preferably made of cryopreservative in the cell medium, is added to the cells in an initial addition step and in at least one subsequent addition step. In each addition step, the concentration of cryopreservative in solution is increased, until a suitable amount of cryopreservative, preferably from about 11.0% to about 16.4% cryopreservative by volume for eukaryotic or aerobic prokaryotic cells, has been absorbed by the cells.

The step-wise treatment begins by forming a suspension of the harvested cells in cell medium containing a first concentration of cryopreservative. After the concentration of the cryopreservative inside and outside the cells substantially equilibrates, the suspension is centrifuged to precipitate the cells and form a cell pellet. At least a portion of the supernatant is then removed. The cells are then resuspended in cell medium containing a second, greater, concentration of the cryopreservative. In preferred embodiments, the concentration of cryopreservative is doubled with each subsequent addition. The concentration of the cryopreservative inside and outside the cells is again caused to substantially equilibrate, the cell suspension again centrifuged, and at least a portion of the supernatant again removed. The suspension, equilibration, and resuspension steps are repeated until the cells have absorbed the predetermined amount of cryopreservative.

The final cell suspension is then frozen. In some embodiments, the suspension is first transferred to a freezer to begin a gradual freezing process and, subsequently, transferred to a liquid nitrogen tank for long term storage.

When the frozen cells are needed, the cell suspension is removed from the liquid nitrogen tank and submerged in a water bath until the cell suspension reaches a desired temperature. Once the cell suspension has been warmed, the cryopreservative is removed from the cell suspension using another step-wise process.

Similar to the process of adding the cryopreservative, the removal of the cryopreservative from the cell suspension is performed in a step-wise manner in which an initial aqueous cryopreservative solution, preferably cryopreservative in the cell medium, is added to the cells, where the concentration of cryopreservative in the initial cryopreservative solution is less than the concentration of cryopreservative in the cells. Next, at least one subsequent cryopreservative solution is added to the cells, where the concentration of cryopreservative is further decreased, in some embodiments by approximately one-half, for each subsequent cryopreservative solution. Lastly, cell medium containing no cryopreservative is added to the cells so that the final concentration of cryopreservative in the cells is negligible.

In preferred embodiments, the cell suspension is centrifuged between addition steps causing the cells to precipitate and form a cell pellet. At least a portion of the supernatant is then removed, the cells are resuspended in cell medium containing a lesser concentration of cryopreservative, and the concentration of cryopreservative inside and outside the cells is substantially equilibrated. These steps are repeated until essentially all the cryopreservative has been removed from the cells.

After removal of the cryopreservative, the cells are transferred to culture dishes and incubated in the cell medium. An advantage of incubation after thawing is that it provides a defense that aids in the reversal of the cryopreservation stress and the prevention of cell damage from thawing, including reoxygenation. Once the incubation period has ended the cells are ready for use.

The above and other advantages of embodiments of this invention will be apparent from the following more detailed description. It is intended that the above advantages can be achieved separately by different aspects of the invention and that additional advantages of this invention will involve various combinations of the above independent advantages such that synergistic benefits may be obtained from combined techniques.

DETAILED DESCRIPTION OF THE PREFERRED EMBODIMENTS

The method in accordance with the invention is useful in preserving cells obtained from any source including cells obtained from any donor species, organism, organ or tissue and especially useful for the preservation of eukaryote and aerobic prokaryote cells. The cells are initially harvested by any process capable of separating the desired cells from a donor source, such as, for example, an organ or tissue sample. The process of isolating the cells should minimize damage to the cells being isolated, such that a maximum number of usable cells are obtained for later use.

In some embodiments of the instant invention, the cells are harvested at temperatures higher than about 4° C., to maximize the energy state of the cells, so that the cells are maintained in an environment that is similar to their normal environment. In preferred embodiments, the temperature of the donor source is maintained between about 34° C.–38° C., although any temperature which maintains normal cell metabolism and protects the cells against subsequent damage is suitable. In one most preferred embodiment, the temperature is maintained at 37° C. Also in preferred embodiments, cell isolation is accomplished through hydrolytic enzymatic digestion of cells obtained from the donor source, by techniques that are well-known to the skilled artisan.

Once the cells have been harvested, they are preconditioned. Preconditioning aids the preservation process in reversing the damage inflicted through harvesting. Preconditioning of the cells includes the steps of washing the cells, forming a suspension of the cells using a conditioning and cryopreservation medium as a storage solution, and then incubating the cells.

Harvested cells, such as for instance, harvested porcine hepatocyte cells, are suspended in a cell conditioning and cryopreservation medium, recovered from the suspension to affect washing, and, and then resuspended in the cell medium. Washing the cells in this fashion removes enzymes used to digest the connective tissue of the donor source. If the enzymes are not removed, they will continue to digest molecular material, including cellular structure, and thereby damage the cells. Typically, the temperature of the cell medium used to wash and resuspend the cells is equivalent to the temperature of the harvested cells. In preferred embodiments, the cells are washed in cell medium which has been heated to between about 34° C.–38° C. and in a most preferred embodiment, the cell medium is heated to about 37° C. The initial concentration of cells in the cell medium prior to washing and the concentration of the cells when resuspended in the cell medium is generally between about $1.5 \times 10^7$ to about $4 \times 10^7$ cells/ml, preferably, about $2 \times 10^7$ cells/ml.

The cell conditioning and cryopreservation medium used in embodiments of the instant invention is an aqueous solution that contains adenosine, a calcium channel blocker, and sufficient metabolic substrates to maintain cell integrity, viability, and function throughout the cryopreservation and recovery processes. It is an advantage of inventive process that the same cell medium is used during all phases of the cryopreservation process, i.e., cell harvesting, preconditioning, freezing, and thawing. Preferred embodiments of a cell medium are described more fully in co-pending application, entitled, "Cell Preconditioning and Cryopreservation Medium", which is-fully incorporated herein by reference.

In preferred embodiments, adenosine is included, typically, in a concentration ranging from about 2.7 mM to about 3.6 mM. Preferably, the adenosine concentration ranges from about 2.9 mM to about 3.1 mM, and, more preferably, is about 3.0 mM. The adenosine is rapidly converted by the cells into ATP to supply immediate energy to the cells during preconditioning. The medium can also include other cell energy sources, such as saccharides like glucose, or metabolites of glucose, such as pyruvate.

A calcium channel blocker is included in the cell medium to prevent calcium-regulated membrane transport of the adenosine. An example of a preferred calcium channel blocker is verapamil. In one embodiment, verapamil is added to the cell medium in an amount ranging from about 0.04 mM to about 0.07 mM. It is added preferably in an amount ranging from about 0.05 mM to about 0.06 and more preferably in an amount of about 0.05 mM.

The other cell metabolites include nutrients that are easily absorbed into the cells to be preserved. Representative nutrients include one or more amino acids selected from alanine, arginine, asparagine, aspartic acid, cystine, glutamine, glutamic acid, glycine, histidine, isoleucine, leucine, lysine, methionine, phenylalanine, proline, serine, threonine, tryptophan, tyrosine, and valine. Additionally, the cell metabolites preferably include one or more vitamins selected from the group comprising pantothenate, choline chloride, folic acid, inositol, niacinamide, pyridoxal, riboflavin, and thiamine. The concentration of the amino acids is chosen to match the amino acid concentration found in the healthy cytoplasm of the cells to be preconditioned.

Alternatively, the concentration of amino acids in the medium is chosen to be proportional to the metabolic needs of the cells during normal cell metabolism.

In some embodiments, the cell medium includes an inorganic salt. Suitable salt-forming inorganic anions include chloride, phosphate, sulfate, and selenite. Suitable salt-forming inorganic cations include sodium, potassium, magnesium, copper, and zinc cations. And in some embodiments, the cell medium has a concentration of inorganic salts substantially equal to the concentration of inorganic salts found in the in vivo donor cells.

Also in some embodiments, the cell cryopreservation medium contains at least one hormone. Representative hormones include insulin, and preferably bovine pancreas insulin; dexamethasone; leutropic hormone and preferably sheep leutropic hormone; transferrin and preferably human transferrin; somatropin; linoleic acid; and fetal bovine serum.

In some embodiments, the medium also contains a cryopreservative for protecting the cells during freezing and thawing. Preferably, the cryopreservative is DMSO.

It is also preferable for the medium to include a free oxygen radical scavenger to protect the cells from free oxygen radicals produced during reoxygenation after storage. Most preferably, the free oxygen radical scavengers are allopurinol and/or glutathione. Alternatively, the cell salvage medium comprises glycine, glutamine/glutamic acid, and cystine, proteins that are rapidly converted by the cell into glutathione.

The cell medium preferably is buffered with a mild buffer solution having a content and concentration such that the cell medium has a first pH that ranges from about 7.3 to about 7.5 at a temperature above 35° C. and has a second pH ranging from about 6.3 to about 6.6, preferably form about 6.4 to about 6.5, and most preferably about 6.4, at a temperature below about 4° C. A suitable buffer includes a sodium carbonate buffer, an N-[Hydroxyethyl] piperazine-N'[2-ethananesulfonic acid] ("HEPES") buffer or a combination of the two. Overall, the concentration of all of the components preferably create a solution that is slightly hyperosmolar.

After the cells have been washed and resuspended, the cells are incubated at a temperature of from about 35° C. to about 38° C., preferably, about 37° C., for a time period ranging from about 10 minutes to 48 hours, preferably from about 15 minutes to about 120 minutes, and more preferably about 25 minutes. In some embodiments, the cell medium is oxygenated by bubbling oxygen through the suspension using a gas having an oxygen content of no less than 80 vol. %, for example with a supply of 95% air/5% $CO_2$. In one embodiment, the medium is saturated at a pressure exceeding atmospheric pressure. Incubation allows the cells time to recover from the insults and restore their energy levels, e.g., ATP levels, prior to the cells being frozen.

Upon completion of the incubation period, the cell suspension is transferred to a precooled cryo-bag, or any other container that is suitable for handling cells, and the temperature of the cell suspension reduced prior to the introduction of a cryopreservative. Reduction of the temperature minimizes the toxicity as the cryopreservative is absorbed by the cell, since cell activity is greatly reduced at low temperatures, such as, for example, 3–5° C. In one preferred embodiment, the temperature is reduced to 40° C. Once the temperature is reduced the step-wise addition of the cryopreservative begins.

Any commercially available cryopreservative is suitable for this process. Representative cryopreservatives include DMSO, glycerol, propylene glycol, and other large molecules with a high bonding affinity to water. In one preferred embodiment, DMSO is the cryopreservative. Addition of the cryopreservative is preferably a multi-step process, in which a storage solution, preferably made of cryopreservative in the cell medium, is added to the cells in an initial addition step and in at least one subsequent addition step. In each addition step, the concentration of cryopreservative in solution is increased, until a suitable amount of cryopreservative, preferably from about 11.0% to about 16.4% cryopreservative by volume for eukaryotic or aerobic prokaryotic cells, has been absorbed by the cells.

During the addition of the cryopreservative, the cell medium is maintained at a temperature of from about 2° to about 6° C. In one preferred embodiment, the temperature is maintained at about 4° C. In each step, cell medium containing cryopreservative is gradually added to the cells, while gently agitating the cells, to establish osmotic equilibrium inside and outside of the cells. Once equilibrium is achieved, the cell suspension is transferred to a centrifuge tube and centrifuged, for example, for 1 minute at 600 G, although any period of about 45 seconds to about 3 minutes at about 1000 to about 3000 G is suitable, to precipitate the cells and form a cell pellet. After centrifugation, at least a portion of the resulting supernatant is removed from the tube and the cell pellet resuspended in additional cell medium. With every subsequent addition, the concentration of cryopreservative in the cell medium is increased. This gradual change in the concentration of cryopreservative minimizes osmotic water shifts across the cellular plasma membrane, which in turn, aids in protecting the cells against shrinkage and/or swelling.

In one preferred embodiment, the cryopreservative concentration is approximately doubled with each addition of cryopreservative-containing cell medium. Thus, in the first addition, 50 ml of cell medium containing 3.3% cryopreservative, based on volume, is added to 50 ml of the cell suspension although any amount in the range of from about 20 to about 400 ml of cell medium containing from about 2.7% to 3.9% cryopreservative, based on volume, can be added to from about 20 to about 200 ml of the cell suspension. After osmotic equilibrium is reached, the cell suspension is centrifuged to form a cell pellet, and at least some of the supernatant, in this example, about 87.5 ml is removed, although any amount between about 75 and about 237.5 ml can be removed depending upon the amount of medium originally added.

In the second addition of the cryopreservative, 69.5 ml of cell medium containing 6.6% cryopreservative, based on volume, is added to resuspend the cells, although any amount in the range of from about 55.6 to about 219.5 ml of cell medium containing from about 5.3% to 8.0% cryopreservative, based on volume, is suitable. After osmotic equilibrium is reached, the cell suspension is again centrifuged to form a cell pellet, and at least some of the supernatant, in this example, about, 69.5 ml is removed, although any amount from about 55.6 to about 219.5 ml can be removed depending upon the amount of cell medium in the second suspension.

Finally, in the third addition of the cryopreservative, 12.5 ml of cell medium containing 12% cryopreservative, based on volume, is added to resuspend the cells, although any amount in the range of about 10 to about 15 ml of cell medium containing from about 10% to about 15%, cropreservative based on volume, is suitable.

After the cryopreservative-containing cell medium is added to form the last cell suspension, the cell suspension is transferred back to a pre-cooled cryo-bag and then transferred to a temporary freezer storage. The freezing step is graduated such that the temperature of the cells is reduced in increments until temperature of about −196° C. is ultimately reached. As such, the initial freezing of the cells is at or about −70° C., although any temperature between about −40° to about −90° C. is suitable. The cell suspension is retained in the freezer for a time period sufficient to allow the water inside the cell to penetrate into extracellular space. Typically, a time period ranging from about 1.5 to about 8 hours is suitable. In one preferred embodiment the time period is about 2 hours.

After the initial reduction in temperature, the cell suspension is transferred to temporary vapor storage in a liquid nitrogen tank. The vapor is slightly warmer than the liquid nitrogen and thus cools the cells to the desired temperature of −196° C. Typically, a time period ranging from about 6 to about 48 hours is suitable. In one preferred embodiment, the vapor time period is about 12 hours.

Once cooling in the vapor phase of the liquid nitrogen tank has been completed, the cell suspension is stored in any environment suitable for long-term storage. In one preferred embodiment, the cryo-bag with the cell suspension is transferred into liquid nitrogen.

The cells are thawed, when required for use. To elevate the temperature of the cells in one preferred embodiment, the frozen cryo-bag is submerged in a water bath having a temperature of about 37° C. In this embodiment, the bag is agitated until the temperature of the cell suspension reaches 37° C. In other preferred embodiments, the temperature of the water bath ranges from about 36° C. to about 42° C. and the bag is agitated until the cell suspension reaches about 36° C. to about 38° C.

Similar to freezing, damage can occur as the result of thawing. To minimize or avoid potential damage, the cells are post-conditioned, after the cell suspension reaches the desired temperature. Similar to cell preconditioning, the cell post-conditioning is done to reverse stresses caused by freezing and to prevent cell damage caused by rewarming and reoxygenation. The post-conditioning further comprises the steps of cryopreservative removal and incubation.

After the temperature of the cell suspension has been elevated, the cell suspension is transferred from the cryo-bag into a pre-warmed round bottom container. Typically, temperatures between 35° C.–38° C. are suitable for prewarming the container. In one preferred embodiment, the temperature of the container is prewarmed to 37° C.

Similar to the addition of the cryopreservative, the removal of the cryopreservative concentration is a multi-step process, in which an initial aqueous cryopreservative solution, preferably cryopreservative in the cell medium, is added to the cells, where the concentration of cryopreservative in the initial cryopreservative solution is less than the concentration of cryopreservative in the cells. Next, at least one subsequent cryopreservative solution is added to the cells, where the concentration of cryopreservative is further decreased for each subsequent cryopreservative solution. Lastly, cell medium containing no cryopreservative is added to the cells so that the final concentration of cryopreservative in the cells is negligible. Gradual changes in the intracellular cryopreservative concentrations, such as for example, DMSO concentrations, minimize osmotic water shifts across the cellular plasma membrane, thereby protecting the cells from shrinkage or swelling.

During the removal of the cryopreservative, the cell medium is preferably maintained at a temperature of about 36°–38° C. In a most preferred embodiment, the temperature is maintained at about 37° C. Thus, the multi-purpose cell medium is at the same temperature as the cell suspension. Once equilibrium is achieved, the cell suspension is transferred to a centrifuge tube and centrifuged, for example, for 1 minute at 600 G, although any period from about forty-five seconds to about 3 minutes at about 1000 to about 3000 G is also suitable, to precipitate the cells and form a cell pellet. After centrifugation, at least a portion of the supernatant is removed from the tube and the cell pellet resuspended in additional cell medium. With every subsequent addition, the concentration of cryopreservative in the cell medium is decreased.

In one preferred embodiment, the concentration of cryopreservative is approximately halved with each addition of cryopreservative-containing cell medium. Thus, in the first step, 50 ml of cell medium containing 6.6% cryopreservative, based on volume, is added to 50 ml of the cell suspension, although any amount about in the range of from about 20 to about 400 ml of cell medium containing from about 5.3% to about 8.0% cryopreservative, based on volume, can be added to from about 20 to about 200 ml of the cell suspension. After osmotic equilibrium is reached, the cell suspension is centrifuged to form a cell pellet, and at least some of the supernatant, in this example, about 62.5 ml is removed, although, depending upon the amount initially added, any amount between about 52.5 ml and about 212.5 ml can be removed.

In the second step, 69.5 ml of cell medium containing 3.3% cryopreservative, by volume, is added to resuspend the cells, although any amount in the range of from about 55.6 to about 219.5 ml of cell medium containing from about 2.7% to about 3.9% cryopreservative, by volume, is suitable. After osmotic equilibrium is reached, the cell suspension is again centrifuged to form a cell pellet, and at least some of the supernatant, in this example, about 69.5 ml is removed, although any amount from about 55.6 ml to about 219.5 ml can be removed depend upon the amount of cell medium in the second suspension.

Finally, 50 ml of cell medium containing no cryopreservative. In the final suspension of the cells is added to resuspend the cells, although any amount in the range of from about 25–100 ml is suitable.

Once the cryopreservative has been removed, the cells are transferred into a prewarmed 150 mm culture dish having a temperature of about 37° C., although any temperature in the range of from about 35° to 38° C. is suitable. The cells in the culture dishes are incubated in the presence of a gas having an oxygen content of no less than 80 vol. %, for example with a supply of 95% air/5% $CO_2$. for about 180 minutes, although any period ranging from about 25 to about 360 minutes is also suitable. Incubation of the cells in the multi-purpose cell medium aids the cells in recovering from the insults inflicted during rewarming and reoxygenation. Thus, the incubation time period must be long enough for the cells to take advantage of the various components of the cell medium, e.g., oxygen scavengers, such as allopurinol, which reduce the number of free oxygen radicals in the cell, and substrates, such as adenosine, that restore ATP energy levels to the cell. Once the incubation period is completed, the supernatant is removed and the cells are ready for further use.

The following examples are included to further illustrate the invention. They are not limitations thereon.

EXAMPLES

Example 1
DMEM Control

Porcine hepatocyte cells were harvested at 37° and placed into eight cryo-vials. The temperature of the eight vials was reduced to 4° C. Each vial was divided into two aliquots of $1.8 \times 10^7$ cells in 0.9 ml distilled, deionized water and each aliquot placed in a separate vial. The aliquots were then spun at 600 rpm for 1 minute and the supernatant removed. The resulting cell pellets were resuspended in 1.8 ml DMEM with 10% DMSO under gentle agitation. A cell sample was obtained for viability/morphology testing. The remainder of each cell suspension was transferred into a 2 ml cryo-vial and each cryo-vial was then sealed.

The 2 ml cryo-vials were then transferred to a −70° C. freezer. After two hours, the cryo-vials were transferred to the vapor phase of a liquid nitrogen tank and held for 10–24 hours. Then, the vials were immersed into the liquid phase of the nitrogen tank and stored for 20 days.

After freezing, the cell suspensions were restored by submerging in a 37–42° C. water bath and agitating until each cell suspension was thawed. A second cell sample was obtained for viability/morphology testing. The remainder of each cell suspension was transferred into a separate round bottom glass tube and 3.6 ml of DMEM was added to each suspension under constant gentle agitation. The cell suspensions were then spun at approximately 600 rpm for 1 minute. The resulting supernatant was removed and the cell pellets were resuspended in 1.5 ml of DMEM. Another sample was obtained for viability/morphology testing. The cell suspensions were each then transferred to a small petri dish (35 ml in diameter) and incubated at 37° C. for sixty minutes. A fourth sample was obtained for viability/morphology testing.

Cell viability was tested using a standard.ized typan blue exclusion procedure. Morphology was tested by using light microscopic evaluation. A scoring system from 1–4 for blebbing of viable cells was used. A score of 1 represented almost no blebs. A score of two represented minor blebbing (approximately 25%). A score of 3 represented moderate blebbing (approximately 50%). A score of 4 represents severe blebbing (greater than 75% blebs). The results are reported in Table 2.

Example 2
Cell Medium with a Single Addition of DMSO at Warm Temperatures (Cm Single Warm)

Porcine hepatocyte cells were harvested at 37° C. and placed into eight cryo-vials. Each vial was divided into two aliquots of $1.8 \times 10^7$ cells in 0.9 ml distilled, deionized water and each aliquot placed in a separate vial. The temperature of each aliquot was maintained at approximately 37° C. The aliquots were then spun at 600 rpm for 1 minute and the supernatant removed. The resulting cell pellets were resuspended in 2.7 ml of an oxygenated cell medium in accordance with the invention having the composition shown in Table 1.

TABLE 1

Cell Conditioning and Cryopreservation Medium

| | |
|---|---|
| Sodium Chloride | 115.00 mM |
| Potassium Chloride | 5.00 mM |
| Potassium Phosphate | 3.00 mM |
| Magnesium Sulfate | 1.20 mM |
| Copper Sulfate | $8.90 \times 10^{-8}$ M |
| Zinc Sulfate | $4.38 \times 10^{-11}$ M |
| Sodium Selenite | $3.00 \times 10^{-9}$ M |
| Sodium Bicarbonate | 25.00 mM |
| N-[Hydroxyethyl]piperazine-N'-[2-ethananesulfonic acid] | 10.00 mM |
| l-Alanine | 0.10 mM |
| l-Arginine-HCl | 0.73 mM |
| l-Asparagine | 0.10 mM |
| l-Aspartic Acid | 1.00 mM |
| l-Cystine | 1.00 mM |
| l-Glutamine | 2.00 mM |
| l-Glutamine Acid | 1.00 mM |
| Glycine | 1.00 mM |
| l-Histidine HCl—H$_2$O | 0.28 mM |
| l-Isoleucine | 0.80 mM |
| l-Leucine | 0.80 mM |
| l-Lysine-HCl | 0.80 mM |
| l-Methionine | 0.20 mM |
| l-Phenylalanine | 0.40 mM |
| l-Proline | 0.10 mM |
| l-Serine | 0.40 mM |
| l-Threonine | 0.40 mM |
| l-Tryptophan | 0.13 mM |
| l-Tyrosine | 0.60 mM |
| l-Valine | 0.80 mM |
| d-Calcium Pantothenate | 0.008 mM |
| Choline Chloride | 0.029 mM |
| Folic Acid | 0.009 mM |
| l-Inositol | 0.040 mM |
| Niacinamide | 0.033 mM |
| Pyridoxal-HCl | 0.020 mM |
| Riboflavin | 0.001 mM |
| Thiamine-HCl | 0.012 mM |
| Adenosine | 3.00 mM |
| d-Glucose | 20.00 mM |
| Sodium Pyruvate | 1.00 mM |
| Insulin (Bovine Pancreas) | 273 μ/L |
| Allopurinol | 1.00 mM |
| Glutathione | 3.00 mM |
| Verapamil | 0.051 mM |
| Dexamethasone | 0.00017 mM |
| Leutropic Hormone (Sheep) | 20 μ/L |
| Transferrin (Human) | $1.28 \times 10^{-7}$ M |
| Somatropin | 10 mμ/L |
| Linoleic Acid | 34 mM |
| Fetal Bovine Serum | 10 wt. % |

The samples were transferred into small petri dishes (60 ml diameter) and each sample incubated for twenty-five minutes at 37° C. The samples were then chilled on ice to 4° C. The samples were then transferred into two round bottomed tubes and spun at approximately 600 rpms for 1 minute. The supernatant was removed from each flask.

The cell pellets resuspended in an additional 2.7 ml of the cell medium described in Table 1. Then, under gentle agitation, 0.9 ml of oxygenated cell medium as described in Table 1, along with 20% DMSO was slowly added into each tube. A cell sample was obtained for viability/morphology testing.

The samples were transferred into 2 ml cryo-vials and sealed. The 2 ml cryo-vials were then transferred to a −70° C. freezer. After two hours, the cryo-vials were transferred to the vapor phase of a liquid nitrogen tank and held for 10–24 hours. Then, the vials were immersed into the liquid phase of the nitrogen tank and stored for 20 days. The frozen cell suspensions were restored by submerging in a 37° C. to a 42° C. water bath and agitating until the cell suspensions reached 37° C. A cell sample was obtained for viability/morphology testing.

Then, the cell suspensions were transferred into round bottom glass tubes and 3.6 ml of oxygenated cell medium described in Table 1 together with DMSO having a concentration of 1500 mOsmol/l, slowly added to each suspension under constant gentle agitation. The cell suspensions were spun at approximately 600 rpms for 1 minute. The supernatant was removed and the resulting cell pellets washed in 5 ml of oxygenated cell medium described in Table 1 along with DMSO having a concentration of 900 mOsmol/l. The cell suspensions were again spun at approximately 600 rpm for 1 minute, the supernatant removed, and the cell pellets resuspended in 1.5 ml of oxygenated cell medium described in Table 1. A sample was obtained for viability/morphology testing.

The cell suspensions were transferred into a 35 ml diameter petri dish and incubated at 37° C. for 60 minutes. Samples were again obtained for viability/morphology testing.

Cell viability/morphology tests were performed as described Example 1. The results are reported in Table 2.

Example 3

Cell Medium Multiple Additions of DMSO at Warm Temperatures (Cm Multiple Warm)

Porcine hepatocyte cells were harvested at 37° C. and placed into eight cryo-vials. Each of the eight vials were divided into two aliquots. Each aliquot included $1.8 \times 10^7$ cells in 0.9 ml distilled, deionized water. The temperature of each aliquot was maintained at approximately 37° C. The aliquots were spun at 600 rpm for 1 minute and the supernatant was removed. The samples were resuspended in 2.7 ml of oxygenated cell cryopreservation medium in accordance with the invention having the composition shown in Table 1.

The cell suspensions were transferred into small petri dishes (60 ml diameter). The samples were incubated for twenty-five minutes at 37° C. The samples were then chilled on ice to 4° C. The cell suspensions were transferred into two round bottom tubes and 3.6 ml of cold oxygenated cell medium as described in Table 1, along with 900 mOsmol/l DMSO. The cell suspensions were spun at approximately 600 rpms for 1 minute. A 6.2 ml fraction of the supernatant was removed from each tube and the cell pellet resuspended in the remaining supernatant. At this point the cell concentration was $2 \times 10^7$ cells/ml.

Under gentle agitation, 5.0 ml of cold oxygenated cell medium as described in Table 1 additionally containing 1500 mOsmol/l DMSO was slowly added to each tube. The cell suspensions were spun at approximately 600 rpms for 1 minute. A 5.1 ml fraction of supernatant was removed from each tube and the cell pellets resuspended in the remaining supernatant (cell concentration $2 \times 10^7$ cells/ml). Under gentle agitation, 0.9 ml of oxygenated cold cell medium as described in Table 1 with 13.7 wt. % DMSO was slowly added into each tube (cell concentration $1 \times 10^7$ cells per ml). A cell sample was obtained for viability/morphology evaluation.

The cell suspensions were then transferred into 2 ml cryo-vials and sealed. The cryo-vials were then transferred into a −70° C. freezer. After two hours, cryo-vials were transferred into the vapor phrase of a liquid nitrogen tank for 10 to 24 hours. The cell suspensions were then immersed in liquid nitrogen and stored for 20 days.

The frozen cell suspensions were restored by submerging in a 37° C. to 40° C. water bath and agitating until the cell suspensions (cell concentration $1.8 \times 10^7$ cells in 1.8 ml) reached 37° C. A cell sample was obtained for viability/morphology testing. Then, the cell suspensions were transferred into round bottom glass tubes and 3.6 ml of oxygenated cell medium as described in Table 1 also containing 1500 mOsmol/l DMSO slowly added to each suspension under constant gentle agitation. The cell suspensions were spun at approximately 600 rpms for 1 minute. The supernatant was removed and the cell pellets washed with 5 ml of oxygenated cell medium as described in Table 1 also containing 900 m/Ismail/l. The cell suspensions were spun at approximately 600 rpms for 1 minute, the supernatant removed, and the cell pellets resuspended in 1.5 ml of oxygenated cell medium as described in Table 1, with no DMSO. A sample was obtained for viability/morphology testing.

Then, the samples were transferred into small petri dishes and incubated at 37° C. for 60 minutes. After 60 minutes, another sample was obtained for viability/morphology testing.

The samples were obtained for cell viability/morphology testing according to the procedures described in Example 1. The results are listed on Table 2.

TABLE 2

CELL VIABILITY OF CELLS CRYOPRESERVED FOR 20 DAYS

| METHOD | Viability Before Freezing | Viability After Thawing | Viability After Washing | Viability After Incubation |
|---|---|---|---|---|
| DMEM CONTROL EXAMPLE 1 | 75% | 66% | 72% | 46% |
| CPM SINGLE WARM EXAMPLE 2 | 83% | 81% | 83% | 74% |
| CPM MULTIPLE WARM EXAMPLE 3 | 92% | 86% | 84% | 77% |

Example 4

The procedure described for Examples 1–3 was repeated except that the cells were stored for a period of 7 days in liquid nitrogen. The results are reported on Table No. 3.

TABLE 3

CELL VIABILITY OF CELLS CRYOPRESERVED FOR 7 DAYS

| METHOD | Viability Before Freezing | Viability After Thawing | Viability After Washing | Viability After Incubation |
|---|---|---|---|---|
| DMEM | 79% | 64% | 71% | — |
| CPM SINGLE WARM | 85% | 78% | 82% | — |
| CPM MULTIPLE WARM | 94% | 86% | 86% | — |

Example 5

The procedure described for Examples 1–3 was repeated, except that the cells were stored for a period of 27 days in liquid nitrogen. The results are repeated on Table No. 4.

TABLE 4

CELL VIABILITY OF CELLS CRYOPRESERVED FOR 27 DAYS

| METHOD | Viability Before Freezing | Viability After Thawing | Viability After Washing | Viability After Incubation |
| --- | --- | --- | --- | --- |
| DMEM | 71% | 63% | 69% | 60% |
| CPM SINGLE WARM | 84% | 71% | 77% | 77% |
| CPM MULTIPLE WARM | 92% | 89% | 87% | 81% |

Example 6

The procedure described for Examples 1–3 was repeated except that the cells were stored for a period of 23 days in liquid nitrogen. The results are repeated on Table No. 5.

TABLE 5

CELL VIABILITY OF CELLS CRYOPRESERVED FOR 23 DAYS

| METHOD | Viability Before Freezing | Viability After Thawing | Viability After Washing | Viability After Incubation |
| --- | --- | --- | --- | --- |
| DMEM | 74% | 64% | 72% | 58% |
| CPM MULTIPLE WARM | 85% | 82% | 84% | 78% |
| CPM MULTIPLE WARM | 92% | 92% | 89% | 79% |

Example 7

The procedure described for Example 1–3 was repeated except that the cells were stored for a period of 28 days in liquid nitrogen. The results are repeated on Table No. 6.

TABLE 6

CELL VIABILITY OF CELLS CRYOPRESERVED FOR 28 DAYS

| METHOD | Viability Before Freezing | Viability After Thawing | Viability After Washing | Viability After Incubation |
| --- | --- | --- | --- | --- |
| DMEM | 75% | 66% | 72% | 46% |
| CPM RAPID WARM | 83% | 81% | 83% | 74% |
| CPM TITRATED WARM | 92% | 86% | 84% | 77% |

While the invention has been described in connection with its preferred embodiments, it will be understood that it is not intended to limit this invention thereto, but it is intended to cover all modifications and alternative embodiments falling within the spirit and scope of the invention as expressed in the appended claims.

We claim:

1. A method for preconditioning and cryopreservation of cells harvested from a donor comprising the steps of:
   suspending cells harvested from a donor in a cell conditioning and cryopreservation medium;
   incubating the cell suspension for a period of at least 10 minutes; and then
   freezing the cells;
   where the cell conditioning and cryopreservation medium includes adenosine, a calcium channel blocker, and a cell nutrient matrix comprising a sufficient amount of nutrients to sustain metabolic needs of the harvested cells during the incubation period without producing detectable levels of lactate or substantially depleting the nutrients, so as to maintain the viability of the harvested cell.

2. The method in accordance with claim 1 wherein the cells are eukaryote or aerobic prokaryote cells.

3. The method in accordance with claim 1, wherein the concentration of adenosine is from about 2.7 mM to about 3.6 mM.

4. The method in accordance with claim 1, wherein the calcium channel blocker is verapamil.

5. The method in accordance with claim 4, wherein the concentration of verapamil is from about 0.04 mM to about 0.07 mM.

6. The method in accordance with claim 1 wherein the cell nutrient matrix contains at least one amino acid selected from the group comprising alanine, arginine, asparagine, aspartic acid, cystine, glutamine, glycine, histidine, isoleucine, leucine, lysine, methionine, phenylalanine, proline, serine, threonine, tryptophan, tyrosine, and valine.

7. The method in accordance with claim 1 wherein the cell nutrient matrix contains at least one vitamin selected from the group comprising pantothenate, choline chloride, folic acid, inositol, niacinamide, pyridoxal, riboflavin, and thiamine, and a saccharide.

8. The method in accordance with claim 1 wherein the cells are incubated for a period of from about 15 minutes to about 2 hours.

9. The method in accordance with claim 1 wherein the cells are incubated at a temperature of from about 35° C. and about 38° C.

10. The method in accordance with claim 1 further comprising the step of oxygenating the cell suspension during the incubation period.

11. The method in accordance with claim 10 wherein the cell suspension is oxygenated by bubbling oxygen through the suspension using a gas having an oxygen content of no less than 80 vol. %.

12. The method in accordance with claim 11 further comprising adding a oxygen free radical scavenger to the cell suspension.

13. The method in accordance with claim 12 wherein the oxygen free radical scavenger is allopurinol, glutathione or combinations thereof.

14. The method in accordance with claim 1 further comprising the step of adding a cryopreservative to the cell suspension after incubating and before freezing.

15. The method in accordance with claim 14 wherein the cryopreservative is Dimethyl Sulfoxide (DMSO).

16. The method in accordance with claim 15 further comprising cooling the cell suspension to a temperature of from about 2° C. to about 6° C. after incubation and before adding the DMSO.

17. The method in accordance with claim 1 wherein the cells are harvested from the donor at a temperature of from about 35° C. to about 38° C.

18. A method for preconditioning and cryopreservation of cells harvested from a donor comprising the steps of:
   suspending eukaryote or aerobic prokaryote cells harvested from a donor in a cell conditioning and cryopreservation medium;

incubating the cell suspension for a period of from about 15 minutes to about 2 hours at a temperature of from about 35° C. and about 38° C.;

cooling the cell suspension to a temperature of from about 2° C. to about 6° C.;

adding sufficient Dimethyl Sulfoxide (DMSO) to the cell suspension to cause a DMSO concentration in the cells of from about 11.0% to about 16.4% by volume; and then freezing the cells;

where the cell conditioning and cryopreservative medium includes from about 2.7 mM to about 3.6 mM adenosine, from about 0.04 mM to about 0.07 mM verapamil, and a cell nutrient matrix comprising a sufficient amount of nutrients sustain the metabolic needs of the harvested cells during the incubation period without producing detectable levels of lactate or substantially depleting the nutrients, so as to maintain the viability of the harvested cells.

19. The method in accordance with claim 18 wherein the cells are harvested from the donor at a temperature of from about 35° C. and about 38° C.

20. The method in accordance with claim 18 wherein the cell nutrient matrix contains at least one amino acid selected from the group comprising alanine, arginine, asparagine, aspartic acid, cystine, glutamine, glycine, histidine, isoleucine, leucine, lysine, methionine, phenylalanine, proline, serine, threonine, tryptophan, tyrosine, and valine.

21. The method in accordance with claim 20 wherein the cell nutrient matrix contains at least one vitamin selected from the group comprising pantothenate, choline chloride, folic acid, inositol, niacinamide, pyridoxal, riboflavin, and thiamine, and a saccharide.

22. The method in accordance with claim 21 further comprising the step of oxygenating the cell suspension during the incubation period.

23. The method in accordance with claim 22 wherein the cell suspension is oxygenated by bubbling oxygen through the suspension using a gas having an oxygen content of no less than 80 vol. %.

24. The method in accordance with claim 23 further comprising adding a oxygen free radical scavenger to the cell suspension.

25. The method in accordance with claim 24 wherein the oxygen free radical scavenger is allopurinol, glutathione or combinations thereof.

26. A method for freezing cells comprising the steps of:
suspending harvested cells in a storage solution;
adding a cryopreservative solution to the cells in an initial addition step and in at least on subsequent addition step, where the concentration of cryopreservative in solution is increased for each subsequent addition step, until a predetermined amount of cryopreservative has been absorbed by the cells; and then
freezing the cell suspension.

27. The method in accordance with claim 26 wherein the cells are eukaryote or aerobic prokaryote cells.

28. The method in accordance with claim 26 further comprising precipitating the cells and removing at least some of the resulting supernatant, then resuspending the cells in the course of the subsequent addition step.

29. The method in accordance with claim 26 wherein the concentration of cryopreservative in solution is approximately doubled for each subsequent addition step.

30. The method in accordance with claim 26 further comprising establishing osmotic equilibrium inside and outside of the cells after an addition step.

31. The method in accordance with claim 26 wherein the cryopreservative is Dimethyl Sulfoxide (DMSO) the cells are maintained at a temperature of from about 2° C. to about 6° C. during each addition step, and a concentration of DMSO absorbed in the cells is from about 11.0% to about 16.4% by volume.

32. The method in accordance with claim 31 wherein the concentration of cryopreservative in the initial cryopreservative solution is from about 2.7% to about 3.9%, based on the volume of the cryopreservative solution.

33. A method for freezing cells comprising the steps of:
suspending harvested eukaryote or aerobic prokaryote cells in a storage solution maintained at a temperature of from about 2° C. to about 6° C.;
adding a solution containing Dimethyl Sulfoxide (DMSO) to the cells in an initial addition step and in at least one subsequent addition step, where the concentration of DMSO is approximately doubled for each subsequent addition step;
establishing osmotic equilibrium inside and outside of the cells after at least one of the subsequent addition steps, until the concentration of DMSO in the cells is from about 11.0% to about 16.4% by volume; and then
freezing the cells.

34. The method in accordance with claim 33 further comprising precipitating the cells and removing at least some of the resulting supernatant, then resuspending the cells in the course of the subsequent addition step.

35. The method in accordance with claim 34 wherein the concentration of cryopreservative in the initial cryopreservative solution is from about 2.7% to about 3.9%, based on the volume of the cryopreservative solution.

36. A method for removing a cryopreservative from harvested cells containing the cryopreservative comprising the steps of:
adding an initial cryopreservative solution to a suspension of the harvested cells containing the cryopreservative, where the concentration of cryopreservative in the initial cryopreservative solution is less than the concentration of cryopreservative in the cells;
adding at least one subsequent cryopreservative solution to the cells where the concentration of cryopreservative in the solution is further decreased for each subsequent cryopreservative solution; then
adding an aqueous liquid that contains no cryopreservative to the cells so that the final concentration of cryopreservative in the cells is negligible.

37. The method in accordance with claim 36 wherein the cells are eukaryote or aerobic prokaryote cells.

38. The method in accordance with claim 36 further comprising precipitating the cells and removing at least some of the resulting supernatant, then resuspending the cells in the course of adding at least one subsequent cryopreservative solution.

39. The method in accordance with claim 36 further comprising precipitating the cells and removing at least some of the resulting supernatant, then resuspending the cells in the course of the adding the aqueous liquid.

40. The method in accordance with claim 36 wherein the concentration of cryopreservative in solution is approximately halved for each subsequent addition of cryopreservative solution.

41. The method in accordance with claim 36 further comprising establishing osmotic equilibrium inside and outside of the cells after adding a subsequent cryopreservative solution.

42. The method in accordance with claim 36 wherein the cryopreservative is Dimethyl Sulfoxide (DMSO).

43. A method for removing Dimethyl Sulfoxide (DMSO) from harvested cells containing DMSO comprising the steps of:

adding an initial DMSO solution to a suspension of harvested eukaryote or aerobic prokaryote cells containing DMSO, where the concentration of DMSO in the initial solution is approximately one-half of the concentration of DMSO in the cell;

adding at least one subsequent DMSO solution to the cells where the concentration of DMSO in the solution is decreased by approximately one-half for each subsequent DMSO cryopreservative solution; then adding an aqueous liquid that does not contain DMSO to the cells so that the final concentration of DMSO in the cells is negligible.

44. The method in accordance with claim 43 further comprising precipitating the cells and removing at least some of the resulting supernatant, then resuspending the cells in the course of adding at least one subsequent DMSO solution.

45. The method in accordance with claim 44 further comprising precipitating the cells and removing at least some of the resulting supernatant, then resuspending the cells in the course of adding the aqueous liquid.

46. The method in accordance with claim 45 further comprising establishing osmotic equilibrium inside and outside of the cells after adding a subsequent DMSO solution.

* * * * *

UNITED STATES PATENT AND TRADEMARK OFFICE
CERTIFICATE OF CORRECTION

PATENT NO. : 6,140,123
DATED : October 31, 2000
INVENTOR(S) : Achilles A. Demetriou, Andreas Kamlot and Jacek Rozga It is certified that error appears in the above-identified patent and that said Letters Patent is hereby corrected as shown below:

Column 6,
Line 58, please delete "cystine" and insert therefor -- cysteine --.

Column 7,
Line 26, please delete "glutamine/glutamic acid" and insert therefor -- glutamine, glutamic acid --.
Line 27, please delete "cystine" and insert therefor -- cysteine --.

Column 12,
Table 1, line 10, please delete "l-Alanine" and insert therefor -- L-Alanine --.
Line 11, please delete "l-Arginine-HCl" and insert therefor -- L-Arginine·HCl --.
Lines 11/12, please delete l-Asparagine" and insert therefor -- L-Asparagine --.
Lines 12/13, please delete "l-Aspartic Acid" and insert therefor -- L-Aspartic Acid --.
Line 13, please delete "l-Cystine" and insert therefor -- L-Cysteine --
Line 15, please delete "l-Glutamine Acid" and insert therefor -- L-Glutamic Acid --.
Line 16, please delete "l-Histidine HCl-$H_2O$ and insert therefor -- L-Histidine HCl·$H_2O$ --.
Line 17, please delete "l-Isoleucine" and insert therefor -- L-Isoleucine --.
Line 18, please delete "l-Leucine" and insert therefor -- L-Leucine --.
Lines 18/19, please delete "l-Lysine-HCl" and insert therefor -- L-Lysine·HCl --.
Lines 19/20, please delete "l-Methionine" and insert therefor -- L-Methionine --.
Lines 20/21, please delete "l-Phenylalanine" and insert therefor -- L-Phenylalanine --.
Line 21, please delete "l-Proline" and insert therefor -- L-Proline --.
Lines 21/22, please delete "l-Serine" and insert therefor -- L-Serine --.
Lines 22/23, please delete "l-Threonine" and insert therefor -- L-Threonine --.
Lines 23/24, please delete "l-Tryptophan" and insert therefor -- L-Tryptophan --.
Line 24, please delete "l-Tyrosine" and insert therefor -- L-Tyrosine --.
Line 25, please delete "l-Valine" and insert therefor -- L-Valine --.

Column 16,
Line 24, please delete "cystine" and insert therefor -- cysteine --.
Line 46, please delete "a" and insert therefor -- an --.

UNITED STATES PATENT AND TRADEMARK OFFICE
CERTIFICATE OF CORRECTION

PATENT NO.   : 6,140,123
DATED        : October 31, 2000
INVENTOR(S)  : Achilles A. Demetriou, Andreas Kamlot and Jacek Rozga It is certified that error appears in the above-identified patent and that said Letters Patent is hereby corrected as shown below:

Column 17,
Line 15, between "nutrients" and "sustain", please insert -- to --.
Line 26, please delete the word "cystine" and insert therefor -- cysteine --.
Line 41, please delete "a" and insert therefor -- an --.

Column 18,
Line 55, please delete "the adding" and insert therefore -- adding --.

Signed and Sealed this

Twentieth Day of August, 2002

Attest:

JAMES E. ROGAN
Attesting Officer            Director of the United States Patent and Trademark Office